United States Patent [19]

Satek et al.

[11] Patent Number: 5,108,658
[45] Date of Patent: Apr. 28, 1992

[54] LIGHT METAL OXIDE-BASED AMORPHOUS CONDUCTOR

[75] Inventors: Larry C. Satek, Wheaton; Mark P. Kaminsky, Winfield; Richard E. DeSimone, Batavia, all of Ill.

[73] Assignee: Amoco Corporation, Chicago, Ill.

[21] Appl. No.: 645,541

[22] Filed: Jan. 24, 1991

[51] Int. Cl.$^5$ .............................................. H01B 1/06
[52] U.S. Cl. ..................... 252/518; 252/521
[58] Field of Search .................. 252/518, 521, 315.01; 423/592, 593, 600, 625, 635, 641, 624; 338/34; 174/261, 102 A, 102 SC

[56] References Cited

U.S. PATENT DOCUMENTS 5,051,204  9/1991  Ohsawa et al. ............ 252/518
5,057,244 10/1991  Nitta et al. ................ 252/518

*Primary Examiner*—Josephine Barr
*Attorney, Agent, or Firm*—Frederick S. Jerome; William H. Magidson; Ralph C. Medhurst

[57] ABSTRACT

The invention relates to a light metal oxide-based amorphous electrical conductor which comprises an amorphous ternary composition consisting of alumina, boria, and an oxide of a light metal selected from Group IA and IIA of the Periodic Table of Elements. Amorphous conductors of the present invention can be produced by forming an aqueous composition comprising a source of light metal ions, a source of alumina and a source of boria to form a homogeneous gel, drying the gel to form a superifically dry solid, and calcining the dry solid at a sufficiently high temperature to form an amorphous ternary composition as described above. The conductor is used as an element of a moisture and/or a high temperature sensor.

19 Claims, 2 Drawing Sheets

LIGHT METAL OXIDE-BASED AMORPHOUS CONDUCTOR

BACKGROUND OF THE INVENTION

This invention relates to a light metal oxide-based amorphous solid. More particularly the present invention relates to an amorphous ternary composition consisting of alumina, boria, and an oxide of a light metal selected from Group IA and IIA of the Periodic Table of Elements, forming an electrically conductive solid. The conductor is useful as an element of a moisture and/or high temperature sensor.

Electrically conductive metallic glasses are well known. Conductivity, also, can be imparted to a glassy material by coating the solid material with a conductor, or by incorporation of a conductor into the glassy material. Homogeneous oxide glasses without transition metal dopants, typically, are not conductors. In certain compositions, however, incorporation of multivalent transition metal ions into the structure can form a useful semiconductor.

It is therefore an object of the present invention to provide a light metal oxide-based composition which forms an amorphous solid having electrical conductivity.

SUMMARY OF THE INVENTION

Objects of this invention can be accomplished by a light metal oxide-based conductor comprising an amorphous ternary composition consisting of $Al_2O_3$, $B_2O_3$, and $M_nO$, where M is a light metal selected from Group IA and IIA of the Periodic Table of Elements and n is 1 or 2, which has a composition represented by a zone inside a quadrilateral ABCD with the three oxides components, $Al_2O$, $B_2O_3$ and $M_nO$, being the apexes of a ternary diagram shown in FIG. 1, whereby the side AB and CD are positioned along lines which correspond to $M_nO$ contents of 35% and 15%, respectively, and side BC and AD are on lines which pass the apex of $M_nO$ and on which the ratio $Al_2O_3$ to $B_2O_3$ is 1 to 9 and 1 to 1, respectively.

A conductor according to the present invention can be made by forming an aqueous composition comprising a source of light metal ions, a source of alumina, and a source of boria to form a homogeneous gel, drying the gel to form a superficially dry solid, and calcining the dry solid at a sufficiently high temperature to form an amorphous ternary composition.

DETAILED DESCRIPTION OF THE INVENTION

Figure 1:
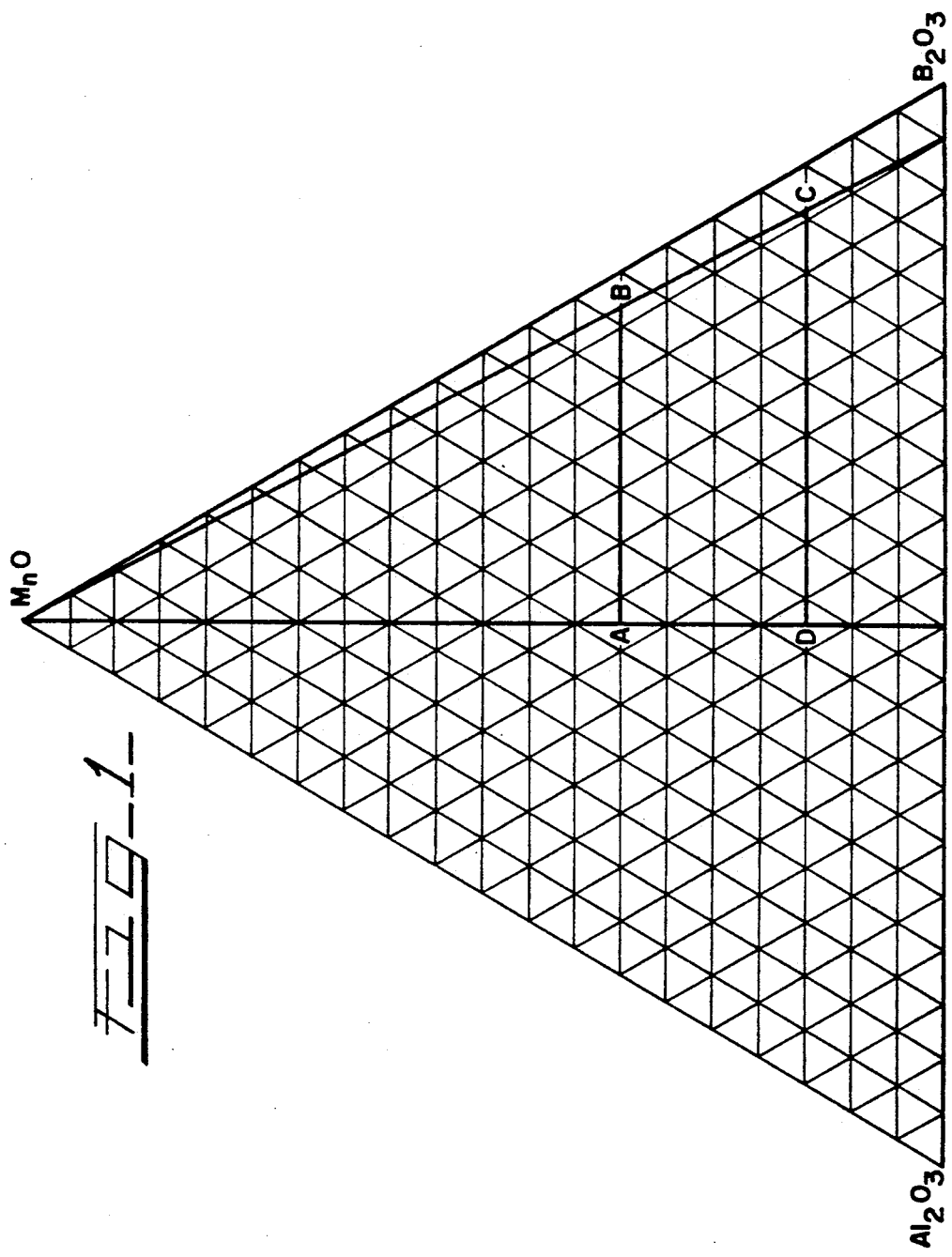
FIG. 1 is a $M_nO/Al_2O_3/B_2O_3$ ternary system composition diagram showing the composition in accordance with the present invention.

The range of composition of the present invention is determined for the following reasons as a result of intensive experiments and trials. First, if $M_nO$ is less than about 15% or if $M_nO$ exceeds about 35% a composition of the present invention does not form. If $M_nO$ is between about 15% and about 35% and the ratio of $Al_2O_3$ to $B_2O_3$ is out of the range of about 1 to 9 to about 1 to 1 the composition does not form.

The composition of the present invention is confirmed to be amorphous by electron diffraction and x-ray diffraction studies. As can be confirmed by the later examples, these light metal oxide-based amorphous solids exhibit electrical conductivity (k) which is defined as the reciprocal of resistivity ($k = 1/\rho$). The terms "resistivity" or "specific resistance" used herein mean a proportionality factor characteristic of different substances equal to the resistance that a centimeter cube of the substance offers to the passage of electricity, the current being perpendicular to two parallel faces. It is defined by the expression:

$$R = \rho(1/A)$$

where R is the resistance of a uniform conductor, l is its length, A is its cross sectional area, and $\rho$ is its resistivity. Resistivity herein is expressed in ohm-centimeters ($\Omega$ Cm).

Typically, amorphous solids of the present invention have a resistivity (specific resistance) in a range downward from about $10^7$ $\Omega$ Cm to about 10 $\Omega$ Cm.

Amorphous solids of the present invention can be produced by the following methods, for example. They can be obtained by forming an aqueous composition comprising a source of light metal ions, a source of alumina and a source of boria to form a homogeneous gel, drying the gel to form a superficially dry solid, and calcining the dry solid at a sufficiently high temperature to form an amorphous ternary composition as described above. The term "light metal" used herein means an element selected from Group IA and Group IIA of the Periodic Table of Elements, page 874, Webster's Ninth New Collegiate Dictionary, Merriam-Webster Incorporated Springfield, Mass., U.S.A. (1984).

Preferred are lithium ($Li^{+I}$), sodium ($Na^{+I}$), potassium ($K^{+I}$), rubidium ($Rb_{+I}$), cesium ($Cs^{+I}$), magnesium ($Mg^{+II}$), calcium ($Ca^{+II}$), strontium ($Sr^{+II}$), and barium ($Ba^{+II}$) ions with potassium, lithium, and calcium being most preferred.

Suitable sources for light metal ions for use in this invention can be any reasonably soluble salt of a light metal ion or precursor thereof which is at least partially soluble in an aqueous medium. Generally sources of light metal ions include at least one member selected from the group of salts having a formula

MX where X is at least one non-oxidizing anion selected from the group acetate, carbonate, formate, hydroxide, oxide and the like with Group I carbonates, and Groups I and II acetates and carbonates being preferred. However, nitrates, per-chlorates, and per-sulfates and other such oxidizing anions are to be avoided.

Salts useful in preparation of the amorphous solids of the present invention include lithium acetate, sodium acetate, potassium acetate, rubidium acetate, cesium acetate, magnesium acetate, calcium acetate, strontium acetate, barium acetate, lithium carbonate, sodium carbonate, potassium carbonate, rubidium carbonate, cesium carbonate, lithium formate, sodium formate, potassium formate, rubidium formate, cesium formate, magnesium formate, calcium formate, strontium formate, barium formate, lithium hydroxide, sodium hydroxide, potassium hydroxide, rubidium hydroxide, cesium hydroxide, magnesium hydroxide, calcium hydroxide, strontium hydroxide, and barium hydroxide, lithium oxide, sodium oxide, potassium oxide, rubidium oxide, cesium oxide, magnesium oxide, calcium oxide, strontium oxide, and barium oxide. Preferred sources of light metal ions used in the present invention include lithium acetate, sodium acetate, potassium acetate, rubidium acetate, cesium acetate, magnesium acetate, calcium acetate, strontium acetate, barium acetate, lithium carbonate, sodium carbonate, potassium carbonate, rubidium carbonate, and cesium carbonate.

The source of alumina is a material capable of producing alumina such as aluminum acetate, but preferred is a well dispersed, liquid source such as an alumina sol. A particularly suitable source of alumina is PHF alumina sol supplied by American Cyanamid. Aluminum nitrate, aluminum borate, and aluminum alkoxides, however, have been found to be unsuitable for use in this invention as a source of alumina.

The source of boria is a material such as boria, borate, or boric acid with pure boric acid being preferred.

Typically best results are obtained when each of the sources is chosen to reduce the content of foreign anions and cations in the reaction mixture.

Generally, these components can be combined in an aqueous medium in approximately stoichiometric proportions sufficient to provide light metal oxide, alumina, and boria having the mixed metal oxide composition described in FIG. 1. Typically the mole ratios of the various reactants can be varied to produce the light metal oxide, alumina, and boria composition. Specifically the ratios in terms of oxides of the reactants are characterized by being within the quadrilateral ABCD on FIG. 1. Compositions below line CD on FIG. 1, containing less than about 15% $M_nO$, are mostly white rather than black after calcination, non-conductive and, depending on the preparation, often exhibited crystalline phases, particularly aluminum borate. Compositions above line AB on FIG. 1, containing more than than about 35% $M_nO$, also, are mostly white rather than black after calcination, non-conductive and, depending on the preparation, often exhibited crystalline phases, particularly $K_2Al_2B_2O_7$. Compositions outside line AD on FIG. 1, containing more $Al_2O_3$ than represented by the line corresponding to a ratio of $Al_2O_3$ to $B_2O_3$ of about 1 to 1, are mostly white rather than black after calcination, non-conductive and, likely to contain crystalline aluminum borate and/or $K_2Al_2B_2O_7$. Compositions outside line BC on FIG. 1, containing more $B_2O_3$ than represented by the line corresponding to a ratio of $Al_2O_3$ to $B_2O_3$ of about 1 to 9, are mostly white rather than black after calcination, and non-conductive.

In somewhat greater detail a preferred procedure is to dissolve the boria source and disperse the alumina source in water or water and a volatile organic liquid, with mixing in a blender for about 3 to 5 minutes, then add an aqueous sol or solution of a source of light metal ion to the blender followed by gelation. Generally, it is advantageous to enhance gelation by adjustment of pH to a value of about 7 and/or above 7 by admixing with the aqueous mixture a source of chemical base, typically in a liquid medium.

Suitable basis compounds include ammonium hydroxide and alkylammonium hydroxide. Preferred chemical bases include ammonium hydroxide and tetramethyl ammonium hydroxide.

Typically, the pH of the aqueous mixture is in a range from about 7 to about 12. If the reaction medium is too acid or too basic, the desired solid generally will not form or other contaminating phases are formed in addition to the desired product. To some extent the pH of the reaction mixture controls properties of the final calcined amorphous solid material. Preferably, the pH of the reaction mixture is in a range from about 7 to about 10, more preferably about 7 to about 9, in order to gel the reaction mixture.

In one embodiment of the process for forming amorphous solids of the present invention, a homogeneous gel is formed of an aqueous-organic medium comprising a volatile organic liquid having at least partial miscibility with water. Useful volatile organic compounds typically have normal boiling points in a temperature range downward from about 140° C. Suitable organic compounds include alcohols, ethers, aldehydes and ketones having from about 1 to about 5 carbon atoms per molecule, such as methanol, ethanol, 2-propanol, 2-butanol, 2-methyl-2-propanol, 2-propen-1-ol, methoxymethane, methoxyethane, 1-methoxypropane, 2-methoxypropane 2-ethoxypropane, 1,3-dioxane, 1,4-dioxane, propanone, butanone, 3-pentanone, and 2-pentanone, and N,N-dimethylformamide. Of these organic compounds methanol, ethanol, and N,N-dimethylformamide are preferred.

Advantageously, in preparation of amorphous solids of the present invention, the amounts of water and volatile organic liquid used are the least amounts needed to consistently obtain a homogeneous gel. Likewise, suitable ratios of organic liquid to water for each liquid system are best determined experimentally.

The gelled mixture is mildly dried for anywhere from a few hours to a few days at varying temperatures typically about 20° to about 225° C. to form a superficially dry cake which is an amorphous light metal oxide-based aluminum borate precursor. Advantageously the gelled mixture is allowed to air dry usually for about 1 to 3 days followed by vacuum drying typically at a pressure of about 0.3 atmosphere for about 15 to 25 hours at about 100° to about 150° C. with a purge of dry gas such as nitrogen.

The superficially dried solid is calcined at a sufficiently high temperature to form an amorphous ternary composition. Generally, the calcination is conducted at a temperature in a range from about 500° to about 1400° C., preferably in a range from about 600° to about 1200° C., for a reaction time that is sufficient to effect formation of the amorphous conductor. Typically, time of calcination is within a range of about 2 to about 30 hours. Samples of material can be removed during calcination to check the degree of reaction and to determine optimum calcination conditions.

The amorphous solid material can be crushed to a powder or to small particles and extruded, pelletized or made into other forms suitable for its intended use.

EXAMPLES

The following examples serve to give specific illustrations of the practice of this invention, but they are not intended in any way to limit the scope of this invention.

EXAMPLE 1

Potassium carbonate (27.6 g, 0.200 mol) dissolved in 32 mL deionized water, alumina sol (PHF from American Cyanamid) (261.4 g of a 7.8% $Al_2O_3$ sol, 0.200 mol) and boric acid (49.44 g, 0.800 mol) dissolved in 268 mL deionized water were added to a Waring blender. Low and high blender settings were used to agitate the mixture for several minutes. The resulting white gel was placed onto a plastic tray (35×45 cm) to dry for three days. This material was then dried in a vacuum oven overnight at about 118° C., 0.3 atm, with a nitrogen gas flow.

A portion (18.1 g) of the dry solid was placed in an alumina tray (5 cm×12 cm) and four platinum wires were placed across the tray so that the three wires were spaced at 1 cm, 3 cm and 7 cm from the fourth wire. The dry solid was calcined in air according to the following program:

$$120° C. \xrightarrow{2 \text{ hrs}} 165° C. \xrightarrow{4 \text{ hrs}} 830° C. \xrightarrow{8 \text{ hrs}}$$

$$830° C. \xrightarrow{3 \text{ hrs}} 120° C. \longrightarrow 50° C.$$

The material resulting from calcination, identified as Example 1, covered the tray to a depth of approximately ¾ cm. The top surface of the calcined product was a black shiny solid, and under the top surface the calcined product was a dull black solid. The final distances between wires were measured, and the resistance was determined using a Simpson volt-ohm meter (VOM).

| Wire | Distance (cm) | Resistance (ohms) |
|------|---------------|-------------------|
| 1-2  | 0.9           | 4000              |
| 2-3  | 2.3           | 4900              |
| 1-3  | 3.2           | 8300              |
| 2-3  | 3.3           | 8600              |
| 2-4  | 5.6           | 13000             |
| 1-4  | 6.5           | 16800             |

These data show that this calcined solid was a conductor which followed Ohm's Law. The specific resistivity of this calcined solid, calculated from the cross-sectional area and the distance, was about $10^4$ Ω Cm.

EXAMPLES 2 TO 5

Potassium carbonate (34.6 g, 0.25 mol) dissolved in 40 mL of deionized water, boric acid (68.0 g, 1.10 mol) dissolved in 340 mL hot deionized water, and alumina sol (PHF from American Cyanamid, 7.7% $Al_2O_3$ by weight, 265.3 g, 0.200 mol) were mixed in a Waring blender as above in Example 1. Ammonium hydroxide (81 mL) was added with mixing. The resulting gel was air and vacuum dried as above. A portion of the dry solid was calcined to 750° C. according to the following program:

$$120° C. \xrightarrow{2 \text{ hrs}} 165° C. \xrightarrow{4 \text{ hrs}} 750° C. \xrightarrow{8 \text{ hrs}}$$

$$750° C. \xrightarrow{3 \text{ hrs}} 120° C. \longrightarrow RT$$

Portions of the dry solid were calcined in air or in nitrogen at different flow rates. Each product of calcination was a hard, black solid which was determined by X-ray diffraction analysis to be an essentially amorphous material. Resistivity, $\rho$, was calculated from the measured resistance between two platinum wires imbedded into the calcination tray, the measured separation distance between the wires and the cross-sectional area of the material.

| Example Number | Flow Rate. (SCFM) | Resistivity, $\rho$, (Ω Cm) |
|----------------|-------------------|-----------------------------|
| 2              | 0 (air)           | 7000                        |
| 3              | 1 (Nitrogen)      | 5000                        |
| 4              | 7                 | 1600                        |
| 5              | 60                | 450                         |

EXAMPLE 6

Sodium carbonate (29.4 g, 0.283 mol) dissolved in 100 mL deionized water, boric acid (75.5 g, 1.22 mol) dissolved in 378 mL hot deionized water, and alumina sol (PHF from American Cyanamid, 7.7% $Al_2O_3$ by weight, 294.4 g, 0.225 mol) were placed in a Waring blender as above in Example 1. Ammonium hydroxide (75 mL) was added and the mixture was mixed and air and vacuum dried as above. Portions were calcined in an alumina dish (5 cm×12 cm) in air to 750° C. according to the following program:

$$120° C. \xrightarrow{2 \text{ hrs}} 165° C. \xrightarrow{4 \text{ hrs}} 750° C. \xrightarrow{8 \text{ hrs}}$$

$$750° C. \xrightarrow{3 \text{ hrs}} 120° C. \longrightarrow RT$$

The resulting product, identified as Example 6, was a hard, dense, black solid which was determined by X-ray diffraction analysis to be an essentially amorphous material. Platinum wires placed in the tray 5.4 cm apart demonstrated this material was a conductor having a resistivity, $\rho$, of about $2\times10^5$ Ω Cm.

EXAMPLE 7

Rubidium carbonate (46.7 g, 0.202 mol) dissolved in 54 mL deionized water, boric acid (49.4 g, 0.80 mol) dissolved in 268 mL hot deionized water, and alumina sol (PHF from American Cyanamid, 7.8% $Al_2O_3$ by weight, 261.5 g, 0.200 mol) were mixed in a Waring blender as above in Example 1. Ammonium hydroxide (54 mL) was added with mixing. The resulting gel was air and vacuum dried as above. A portion of the dry solid was calcined in an alumina dish (5 cm×12 cm) in air to 830° C. according to the following program:

$$120° C. \xrightarrow{2 \text{ hrs}} 165° C. \xrightarrow{4 \text{ hrs}} 830° C. \xrightarrow{8 \text{ hrs}}$$

$$830° C. \xrightarrow{3 \text{ hrs}} 120° C. \longrightarrow RT$$

The resulting product, identified as Example 7, was a black, hard, dense solid with a few gray patches. The resulting product was determined by X-ray diffraction analysis to be an essentially amorphous material. Platinum wires placed in the tray 4.5 cm apart demonstrated the material was a conductor having a resistivity, $\rho$, of about $5.7\times10^3$ Ω Cm.

EXAMPLE 8

Cesium carbonate (40.7 g, 0.125 mol) dissolved in 47 mL deionized water, boric acid (30.9 g, 0.500 mol) dissolved in 167 mL hot deionized water, and alumina sol (PHF from American Cyanamid, 7.8% $Al_2O_3$ by weight, 163.5 g, 0.125 mol) were mixed in a Waring blender as above in Example 1. Ammonium hydroxide (52 mL) was added to the blender. The resulting gel was air and vacuum dried. A portion of the dry solid was calcined in an alumina dish (5 cm × 12 cm) in air to 830° C. according to the following program:

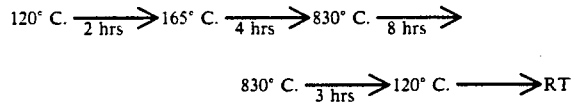

$$830° C. \xrightarrow{3 \text{ hrs}} 120° C. \longrightarrow RT$$

The calcined material, identified as Example 8, was a black, hard, dense solid, with a few gray patches. This product of calcination was determined by X-ray diffraction analysis to be an essentially amorphous material. Platinum wires placed in the tray 4.5 cm apart demonstrated the material was a conductor having a resistivity, $\rho$, of about $9 \times 10^3$ $\Omega$ Cm.

EXAMPLE 9

Lithium acetate (51.0 g, 0.50 mol) dissolved in 50 mL deionized water, boric acid (67.98 g, 1.10 mol) dissolved in 223 mL hot deionized water, and alumina sol (PHF from American Cyanamid, 8.56% Al$_2$O$_3$ by weight, 238.3 g, 0.200 mol) were mixed in a Waring blender as above in Example 1. Ammonium hydroxide (25 mL) was added to the mixture in the blender. The resulting gel was air and vacuum dried. A portion of the dry solid was calcined in an alumina dish (5 cm × 12 cm) in nitrogen (60 SCFH) to 800° C. according to the following program:

$$120° C. \xrightarrow{2 \text{ hrs}} 165° C. \xrightarrow{4 \text{ hrs}} 800° C. \xrightarrow{8 \text{ hrs}}$$

$$800° C. \longrightarrow RT$$

The resulting product, identified as Example 9, was a grayish-black solid. Platinum wires placed in a tray 4.8 cm apart demonstrated the material was a conductor having a resistivity, $\rho$, of about $1.6 \times 10^2$ $\Omega$ Cm.

EXAMPLES 10 AND 11

Magnesium acetate tetrahydrate (19.1 g, 0.0891 mol) and boric acid (22 g, 0.356 mol) were dissolved in hot deionized water, mixed together and added to Al$_2$O$_3$ (PHF from American Cyanamid, 7.8% Al$_2$O$_3$, 116 g, 0.0887 mol) in a Waring blender at room temperature. Mixing is started and maintained for around 30 sec at which point aqueous NH$_3$ (9 mL) was added to gel the mixture. Mixing continued by hand until the gel was smooth. The gel was then spread out in a thin layer (⅛ in) to dry.

Calcination of a portion of the air-dried solid in air at 750° C. for 8 hrs produced a black/gray weakly conducting solid which was identified as Example 10. Calcination of another portion of the air-dried solid in nitrogen produced a black solid, identified as Example 11, having a resistivity, $\rho$, in the mega-ohm range.

EXAMPLES 12 AND 13

Calcium acetate hydrate (15.5 g, 0.0875 mol) in 50 mL deionized water and boric acid (33 g, 0.534 mol) in 320 mL hot deionized water were mixed together and added to Al$_2$O$_3$ (PHF from American Cyanamid, 7.8% Al$_2$O$_3$, 116 g, 0.0887 mol) in a Waring blender at room temperature. Mixing was started and maintained for around 30 sec at which point aqueous NH$_3$ (9 mL) was added to gel the mixture. Mixing continued by hand until the gel was smooth. The gel was then spread out in a thin layer to dry.

Calcination of a portion of the air-dried solid, identified as Example 12, in air yielded a charcoal grey having a resistivity, $\rho$, in the mega-ohm range.

Calcination of another portion of the air-dried gel in a nitrogen atmosphere (2 hrs. to 500° C., 3 hrs to 1000° C., hold for 10 min, then cool to room temperature) yielded a black, conducting material, identified as Example 13 having a resistivity, $\rho$, of about $7.5 \times 10^2$ $\Omega$ Cm.

EXAMPLE 14

Potassium carbonate (17.1 g, 0.124 mol) dissolved in 20 mL deionized water, boric acid (34.0 g, 0.550 mol) dissolved in 170 mL hot deionized water, alumina sol (PHF from American Cyanamid, 7.7% Al$_2$O$_3$ by weight, 132.7 g, 0.100 mol) and rhodium (III) chloride trihydrate (0.66 g, 2.51 mmol) dissolved in 10 mL deionized water were mixed in a Waring blender as above in Example 1. The pH of the mixture was 0.6. The resulting gel was air and vacuum dried as above. Portions of the dry solid were calcined in an alumina dish (5 cm × 12 cm) in air to 750° C. according to the following program:

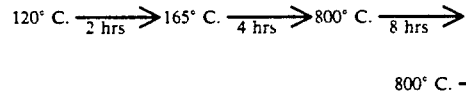

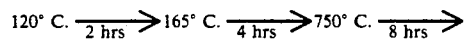

The resulting product of calcination, identified as Example 14, was a hard, foam-like, black solid having a gray tint. Platinum wires placed in the tray 5.3 cm apart demonstrated the material was a conductor having a resistivity, $\rho$, of about $1.5 \times 10^4$ $\Omega$ Cm.

EXAMPLE 15

Potassium carbonate (34.2 g, 0.248 mol) dissolved in 40 mL deionized water, boric acid (68.0 g, 1.10 mol) dissolved in 340 mL hot deionized water, alumina sol (PHF from American Cyanamid, 7.7% Al$_2$O$_3$ by weight, 265.7 g, 0.200 mol) and platinum (IV) chloride solution (5.85 g of a 4.0% solution, 1.2 mol) were mixed in a Waring blender. Ammonium hydroxide (75 mL) was added and the mixture was mixed as above. The pH of the mixture was 9.2. The resulting gel was air and vacuum dried as above. Portions of the dry solid were calcined in an alumina dish (5 cm × 12 cm) in air to 750° C. according to the following program:

$$120° C. \xrightarrow{2 \text{ hrs}} 165° C. \xrightarrow{4 \text{ hrs}} 750° C. \xrightarrow{8 \text{ hrs}}$$

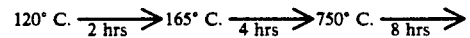

The resulting product of calcination, identified as Example 15, was a hard, foam-like, black solid. This product of calcination was determined by X-ray diffraction analysis to be an essentially amorphous material. Platinum wires placed in the tray 5.4 cm apart demonstrated the material was a conductor having a resistivity, $\rho$, of about $2.7 \times 10^3$ $\Omega$ Cm.

EXAMPLE 16

Potassium carbonate (27.64 g, 0.200 mol) dissolved in 32 mL deionized water, boric acid (49.4 g, 0.80 mol) dissolved in 268 mL hot deionized water, alumina sol (PHF from American Cyanamid, 7.8% $Al_2O_3$ by weight, 236.0 g, 0.181 mol) and colloidal silica (3.53 g of a 34% $SiO_2$ by weight, 0.020 mol) were mixed into a Waring blender. Ammonium hydroxide (50 mL) was added. The pH of the mixture was 10. The resulting gel was dried as above. A portion of the dry solid was calcined in an alumina dish (5 cm × 12 cm) in air to 750° C. according to the following program:

$$120° C. \xrightarrow{2 \text{ hrs}} 165° C. \xrightarrow{4 \text{ hrs}} 750° C. \xrightarrow{8 \text{ hrs}}$$

$$750° C. \xrightarrow{3 \text{ hrs}} 120° C. \longrightarrow RT$$

The resulting product of calcination, identified as Example 16, was a hard, foam-like, black solid. This product of calcination was determined by X-ray diffraction analysis to be an essentially amorphous material. Platinum wires placed in the tray 5.2 cm apart demonstrated the material was a conductor having a resistivity, $\rho$, of about $3 \times 10^4$ Ω Cm.

EXAMPLE 17

Potassium carbonate (27.64 g, 0.200 mol) dissolved in 32 mL deionized water, boric acid (49.4 g, 0.80 mol) dissolved in 268 mL hot deionized water, alumina sol (PHF from American Cyanamid, 7.8% $Al_2O_3$ by weight, 258.9 g, 0.199 mol) and magnesium carbonate (0.34 g, 4.0 mol) were mixed in a Waring blender. Ammonium hydroxide (54 mL) was added and the mixture was mixed as above. The pH of the mixture was 10.5. The resulting gel was air and vacuum dried as above. A portion of the dry solid was calcined in an alumina dish (5 cm × 12 cm) in air to 750° C. according to the following program:

$$120° C. \xrightarrow{2 \text{ hrs}} 165° C. \xrightarrow{4 \text{ hrs}} 750° C. \xrightarrow{8 \text{ hrs}}$$

$$750° C. \xrightarrow{3 \text{ hrs}} 120° C. \longrightarrow RT$$

The resulting product of calcination, identified as Q Example 17, was a hard, foam-like, black solid. This product of calcination was determined by X-ray diffraction analysis to be an essentially amorphous material. Platinum wires placed in the tray 4.0 cm apart demonstrated the material was a conductor having a resistivity, $\rho$, of about $3 \times 10^3$ Ω Cm.

EXAMPLE 18

Figure 2:
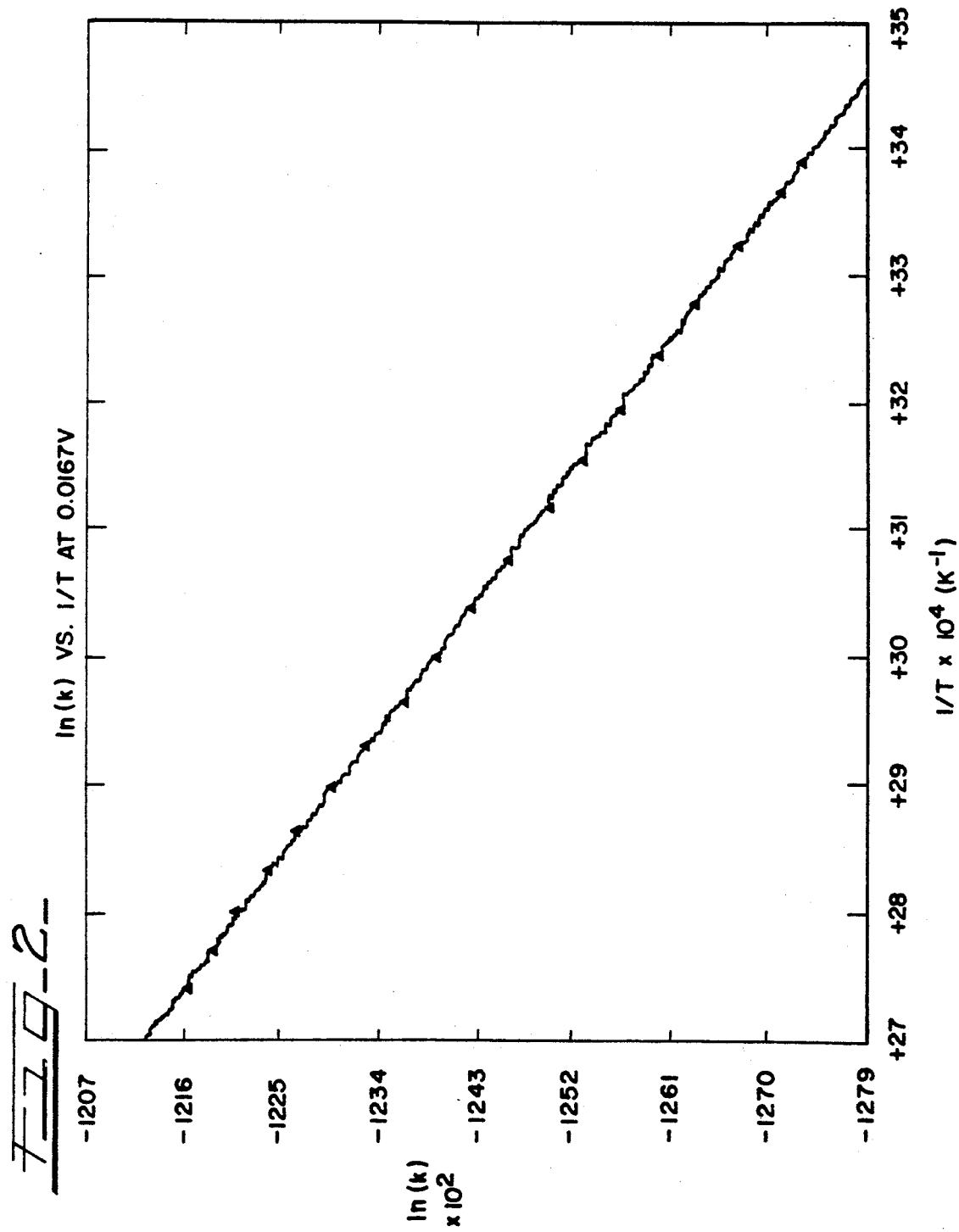
FIG. 2 is a diagram showing changes in conductivity with temperature for an example of a composition of the present invention.

FIG. 2 shows the temperature dependence of electrical conductivity for a sample prepared in a manner similar to Example 1.

COMPARATIVE EXAMPLE A

Potassium carbonate (13.8 g, 0.100 mol) boric acid (24.7 g, 0.400 mol) aluminum nitrate hydrate (75.2 g, 0.200 mol) were placed into a porcelain mortar, mixed and ground to a white powder. A portion was calcined in an alumina dish (5 cm × 12 cm) in air to 830° C. according to the following program:

$$120° C. \xrightarrow{2 \text{ hrs}} 165° C. \xrightarrow{4 \text{ hrs}} 830° C. \xrightarrow{8 \text{ hrs}}$$

$$830° C. \xrightarrow{3 \text{ hrs}} 120° C. \longrightarrow RT$$

The resulting product of calcination, identified as Comparative Example A, was a white chunky material. This product of calcination was determined by X-ray diffraction analysis to contain crystalline material including $K_2Al_2B_2O_7$. The chunks had some yellow coating in places. Platinum wires placed in the tray 5.4 cm apart demonstrated the material was not a conductor.

COMPARATIVE EXAMPLE B

Potassium carbonate (13.8 g, 0.100 mol) dissolved in 16 mL deionized water, boric acid (24.7 g, 0.400 mol) dissolved in 134 mL hot deionized water, and aluminum nitrate hydrate, (75.2 g, 0.200 mol) dissolved in 17 mL warm deionized water were mixed in a Waring blender. Ammonium hydroxide (58 mL) was added and the mixture was mixed as above. The resulting gel was air and vacuum dried as above. Portion of the dry solid were calcined in an alumina dish (5 cm × 12 cm) in air to 830° C. according to the following program:

$$120° C. \xrightarrow{2 \text{ hrs}} 165° C. \xrightarrow{4 \text{ hrs}} 830° C. \xrightarrow{8 \text{ hrs}}$$

$$830° C. \xrightarrow{3 \text{ hrs}} 120° C. \longrightarrow RT$$

The resulting product of calcination, identified as Comparative Example B was a white clump mass with a pale sea green glaze. This product of calcination was determined by X-ray diffraction analysis to contain crystalline material including $K_2Al_2B_2O_7$. Platinum wires placed in the tray 5.0 cm apart demonstrated the material was not a conductor.

COMPARATIVE EXAMPLE C

Potassium carbonate (27.6 g, 0.200 mol) dissolved in 32 mL deionized water, boric acid (49.4 g, 0.800 mol) dissolved in 268 mL hot deionized water, and aluminum s-butoxide, (95% from Alfa Products, 103.6 g, 0.400 mol) were mixed in a Waring blender. Ammonium hydroxide (52 mL) was added and the mixture was mixed as above. The pH of the mixture was 10. The resulting gel was air and vacuum dried as above. Portions of the dry solid were calcined in an alumina dish (5 cm × 12 cm) in air to 830° C. according to the following program:

$$120° C. \xrightarrow{2 \text{ hrs}} 165° C. \xrightarrow{4 \text{ hrs}} 830° C. \xrightarrow{8 \text{ hrs}}$$

$$830° C. \xrightarrow{3 \text{ hrs}} 120° C. \longrightarrow RT$$

The resulting product of calcination, identified as Comparative Example C was white chunks having a light blue-gray hue. Platinum wires placed in the tray 4.9 cm apart demonstrated that this material was not a conductor.

That which is claimed is:

1. An electrical conductor comprising an amorphous ternary composition consisting of $Al_2O_3$, $B_2O_3$, and $M_nO$ where M is a light metal selected from Group IA and IIA of the Periodic Table of Elements and n is 1 or 2, wherein the composition of ternary components is within a quadrilateral ABCD using the three oxides $Al_2O_3$, $B_2O_3$, and $M_nO$ as apexes of a ternary diagram, the side AB being positioned on a line corresponding to constant $M_nO$ content of 35%, the side BC being positioned on a line which passes the apex of $M_nO$ and on which the ratio of $Al_2O_3$ to $B_2O_3$ is 1 to 9, the side CD being positioned on a line corresponding to constant $M_nO$ content of 15%, the side AD being positioned on a line which passes the apex of $M_nO$ and on which the ratio of $Al_2O_3$ to $B_2O_3$ is 1 to 1.

2. A conductor according to claim 1 made by forming an aqueous composition comprising a source of light metal ions, a source of alumina, and a source of boria to form a homogeneous gel, drying the gel to form a superficially dry solid, and calcining the dry solid at a temperature in a range upward from about 500° C. to form an amorphous ternary composition, wherein the source of light metal ions is at least one member selected from the group consisting of salts having a formula

MX where M is a light metal selected from the group consisting of Group IA and Group IIA of the Periodic Table of Elements and X is at least one non-oxidizing anion selected from the group consisting of acetate, carbonate, formate, hydroxide, and oxide, the source of alumina is at least one member selected from the group consisting of aluminum acetate and alumina sol, and the source of boria is boric acid.

3. A conductor according to claim 2 wherein X is selected from the group consisting of acetate, carbonate, hydroxide, and oxide.

4. A conductor according to claim 3 wherein the calcination is conducted at temperatures in a range from about 500° C. to about 1400° C.

5. A conductor according to claim 3 wherein M is a light metal selected from the group consisting of lithium, sodium, potassium, rubidium, cesium, magnesium, calcium, strontium, and barium ions.

6. A conductor according to claim 3 wherein the source of alumina is an alumina sol, and the source of light metal ions is at least one member selected from the group consisting of lithium acetate, and lithium carbonate.

7. A conductor according to claim 6 wherein the calcination is conducted at temperatures in a range from about 600° C. to about 1200° C.

8. A conductor according to claim 3 wherein the source of alumina is an alumina sol, and the source of light metal ions is at least one member selected from the group consisting of sodium acetate, and sodium carbonate.

9. A conductor according to claim 8 wherein the calcination is conducted at temperatures in a range from about 600° C. to about 1200° C.

10. A conductor according to claim 3 wherein the source of alumina is an alumina sol, and the source of light metal ions is at least one member selected from the group consisting of potassium acetate, and potassium carbonate.

11. A conductor according to claim 10 wherein the calcination is conducted at temperatures in a range from about 600° C. to about 1200° C.

12. A conductor according to claim 3 wherein the source of alumina is an alumina sol, and the source of light metal ions is at least one member selected from the group consisting of potassium acetate, and potassium carbonate.

13. A conductor according to claim 12 wherein the calcination is conducted at temperatures in a range from about 600° C. to about 1200° C.

14. A conductor according to claim 3 wherein the source of alumina is an alumina sol, and the source of light metal ions is at least one member selected from the group consisting of cesium acetate, and cesium carbonate.

15. A conductor according to claim 14 wherein the calcination is conducted at temperatures in a range from about 600° C. to about 1200° C.

16. A conductor according to claim 3 wherein the source of alumina is an alumina sol, and the source of light metal ions is at least one member selected from the group consisting of magnesium acetate, and magnesium carbonate.

17. A conductor according to claim 16 wherein the calcination is conducted at temperatures in a range from about 600° C. to about 1200° C.

18. A conductor according to claim 3 wherein the source of alumina is an alumina sol, and the source of light metal ions is at least one member selected from the group consisting of calcium acetate, and calcium carbonate.

19. A conductor according to claim 18 wherein the calcination is conducted at temperatures in a range from about 600° C. to about 1200° C.

* * * * *

UNITED STATES PATENT AND TRADEMARK OFFICE
CERTIFICATE OF CORRECTION

PATENT NO. : 5,108,658

DATED : April 28, 1992

INVENTOR(S) : Larry C. Satek, et al

It is certified that error appears in the above-identified patent and that said Letters Patent is hereby corrected as shown below:

| Column | Line(s) | |
|---|---|---|
| 9 | 49 | printed text reading "identified as Q Example 17" should read --identified as Example 17-- |
| 12 | 23 | printed text reading "consisting of potassium acetate, and potassium carbonate" should read --consisting of rubidium acetate, and rubidium carbonate-- |

Signed and Sealed this

Thirteenth Day of July, 1993

Attest:

MICHAEL K. KIRK

*Attesting Officer*  Acting Commissioner of Patents and Trademarks